(12) United States Patent
Nguyen et al.

(10) Patent No.: US 8,043,257 B2
(45) Date of Patent: Oct. 25, 2011

(54) AGENT DELIVERY CATHETER HAVING AN INFLATION BRIDGE BETWEEN TWO AXIALLY SPACED BALLOONS

(75) Inventors: Binh T. Nguyen, Newark, CA (US); Randolf von Oepen, Los Altos, CA (US); Kevin J. Ehrenreich, San Francisco, CA (US); William E. Webler, Jr., San Jose, CA (US); Sung Woo Min, Mountain View, CA (US); Rommel Lumauig, San Jose, CA (US); Travis R. Yribarren, Campbell, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 221 days.

(21) Appl. No.: 12/328,054

(22) Filed: Dec. 4, 2008

(65) Prior Publication Data
US 2009/0204068 A1    Aug. 13, 2009

Related U.S. Application Data

(60) Provisional application No. 60/992,983, filed on Dec. 6, 2007.

(51) Int. Cl.
*A61M 29/00* (2006.01)
(52) U.S. Cl. ................. 604/101.01; 604/101.03
(58) Field of Classification Search ........... 604/96.01, 604/101.01, 101.03, 101.05, 102.02, 102.03, 604/103.01, 103.02, 544, 99.04; 623/1.11; 606/194

See application file for complete search history.

(56) References Cited

U.S. PATENT DOCUMENTS

| | | | |
|---|---|---|---|
| 5,415,634 A * | 5/1995 | Glynn et al. | 604/103.08 |
| 5,599,294 A | 2/1997 | Edwards et al. | |
| 5,919,163 A * | 7/1999 | Glickman | 604/101.05 |
| 6,030,362 A * | 2/2000 | Boussignac et al. | 604/101.01 |
| 7,273,469 B1 | 9/2007 | Chan et al. | |
| 2002/0072706 A1 | 6/2002 | Hiblar et al. | |
| 2005/0203462 A1* | 9/2005 | Katoh et al. | 604/164.1 |

FOREIGN PATENT DOCUMENTS

| | | |
|---|---|---|
| DE | 102006003181 A1 | 7/2007 |
| WO | 9210142 A | 6/1992 |

* cited by examiner

*Primary Examiner* — Christopher D Koharski
(74) *Attorney, Agent, or Firm* — Fulwider Patton LLP; Randy Shen; Thomas H. Majcher (57) ABSTRACT

An agent delivery catheter having two or more axially spaced balloons and an inflation bridge providing fluid communication between the two balloons. The catheter generally has a proximal balloon, a distal balloon, and a tube defining an inflation bridge lumen which is located in part within the inflatable interiors of the balloons, and which extends therebetween, and which has a proximal port within the proximal balloon interior and a distal port within the distal balloon interior to thereby provide for inflation of the distal balloon by placing the distal balloon interior in fluid communication with the proximal balloon interior of the shaft.

16 Claims, 4 Drawing Sheets

AGENT DELIVERY CATHETER HAVING AN INFLATION BRIDGE BETWEEN TWO AXIALLY SPACED BALLOONS

CROSS-REFERENCES TO RELATED APPLICATIONS

This application claims priority to U.S. provisional application No. 60/992,983, filed Dec. 6, 2007.

BACKGROUND OF THE INVENTION

The invention relates to the field of medical devices, and more particularly to catheters, such as needle catheters or other elongated devices configured for inserting into a patient's body lumen to perform a diagnostic or therapeutic procedure, such as delivery of an agent to the coronary or peripheral vasculature.

The delivery of therapeutic agents into various parts of the vascular system has been shown to be an effective method of treating vascular disease. A variety of agents can be delivered including anti-proliferative, anti-inflammatory, anti-neoplastic, anti-platelet, anti-coagulant, anti-fibrin, anti-thrombotic, anti-mitotic, antibiotic, anti-allergic, and antioxidant compounds. To treat a diseased section of the vessel, these agents could be delivered directly into the vessel wall adjacent to the diseased section, and/or into the perivascular space. Vascular regenerative therapies, such as the delivery of mesenchymal stem cells, require the delivery of a bolus of biologic materials into a portion of the vascular system such as into the tissue surrounding a coronary vessel. Local, as opposed to systemic delivery is a preferred method of treatment in that smaller total levels of medication are administered in comparison to systemic dosages yet are concentrated at a specific site. As a result, local delivery produces fewer side effects and achieves more effective results.

A variety of methods and devices have been proposed for percutaneous drug delivery to a diseased region of the vasculature, including catheters having a needle configured to be directed out of the catheter and into the vessel wall to deliver the desired agent to the tissue. In order to properly position the distal end of a drug delivery catheter in a patient's tortuous distal vasculature, the catheter should preferably have a low-profile, flexible distal section despite also having the necessary structural components required for the drug delivery at the operative distal end of the catheter. However, these are often competing considerations, making it difficult to provide the necessary operative distal end while still having good deliverability (i.e., ability to track within the patient's often tortuous vasculature to a desired location therein).

SUMMARY OF THE INVENTION

The invention is directed to an agent delivery catheter having two or more axially spaced balloons and an inflation bridge providing fluid communication between the two balloons. A catheter of the invention generally has a proximal balloon, a distal balloon, and a tube defining an inflation bridge lumen which is located in part within the inflatable interiors of the proximal and distal balloons, and which extends therebetween, and which has a proximal port within the proximal balloon interior and a distal port within the distal balloon interior to thereby provide for inflation of the distal balloon by placing the distal balloon interior in fluid communication with the proximal balloon interior of the shaft.

In a presently preferred embodiment, a catheter of the invention is a needle catheter having a needle which is slidably disposed in a needle-through lumen of the catheter shaft, and which has a retracted configuration, and an extended configuration with the needle extending through a needle-through port of the needle-through lumen for delivering an agent to an injection site in a wall of the patient's body lumen. The balloons are on either end of the needle-through port, and the inflation bridge tube extending between the balloons therefore extends from a location proximal to a location distal of the needle-through port of the catheter shaft.

At least part of the length of the inflation bridge tube is on an outer surface of the shaft, optionally at least partially embedded in the shaft. The inflation bridge tube extends within at least a portion of the inflatable interior of each balloon, and in a presently preferred embodiment it extends helically through substantially the entire length (i.e., all or at least a majority of the length) of the inflatable interior of each balloon. Ports in the ends of the tube and/or through a sidewall of the tube allow inflation fluid from the inflation lumen of the shaft to flow into the inflation bridge tube lumen and then out of the inflation bridge tube lumen into the distal balloon interior. However, in a presently preferred embodiment, the inflation bridge tube is configured to prevent or minimize the risk of the tube causing some form of damage to (e.g., perforating) the balloon or the patient's anatomy. Additionally, the inflation bridge tube is preferably configured to provide for relatively fast transfer of inflation fluid to the distal balloon, while nonetheless providing ease of manufacture of a highly flexible, deliverable catheter. These and other advantages of the invention will become more apparent from the following detailed description of the invention and accompanying exemplary drawings.

DETAILED DESCRIPTION OF THE PREFERRED EMBODIMENTS

Figure 1:
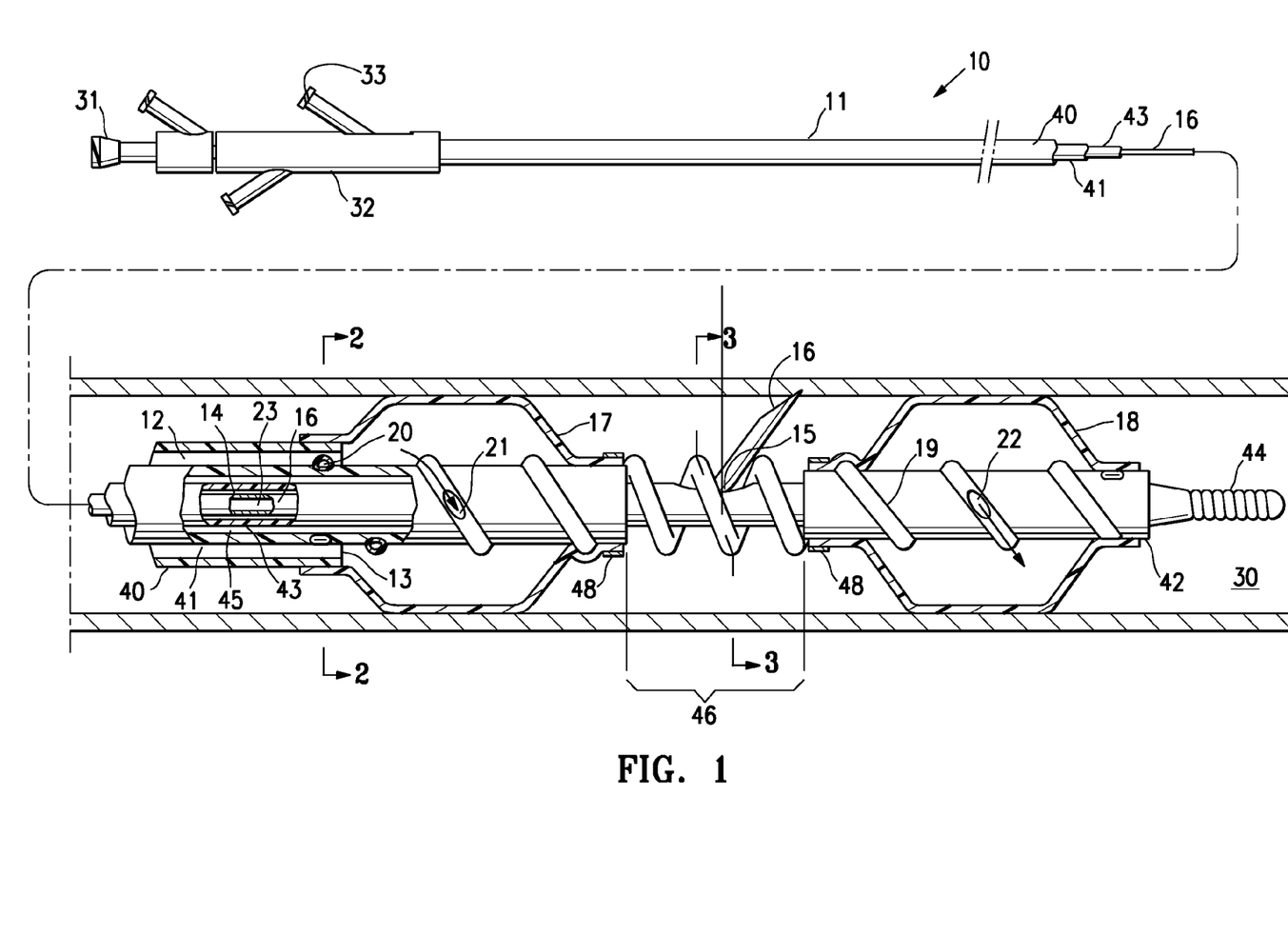
FIG. 1 is an elevational view, partially in section of a needle catheter embodying features of the invention having a proximal and a distal balloon, and an inflation bridge tube extending helically therebetween.

FIG. 1 illustrates an elevational, partially in section, view of an agent delivery catheter 10 embodying features of the invention, generally comprising an elongated catheter shaft 11 having a proximal end, a distal end, a distal shaft section, an inflation lumen 12 extending distally from the proximal end of the shaft to a distal end 13 located proximal to a distal end of the catheter, a needle-through lumen 14 slidably containing a hollow needle 16 therein, and at least one needle-through port 15, and a proximal balloon 17 on the distal shaft section with an inflatable interior located proximal to the needle-through port 15, and a distal balloon 18 which is on the shaft distal to the proximal balloon and which has an inflatable interior located distal to the needle-through port 15, and a tube 19 defining an inflation bridge lumen 20, extending between the inflatable interiors of the balloons 17, 18 from a location proximal to a location distal of the needle-through port 15. The proximal balloon 17 is sealingly secured to the shaft 11 adjacent to the distal end 13 of the inflation lumen 12 such that the proximal balloon inflatable interior is in fluid communication with the inflation lumen 12. The inflation bridge tube 19 has a proximal port 21 within the proximal balloon interior, and a distal port 22 within the distal balloon interior to thereby provide for inflation of the distal balloon 18 by placing the distal balloon interior in fluid communication with the proximal balloon interior. A proximal handle assembly 32 at the proximal end of the catheter is configured for connecting to fluid sources (for flowing agent, balloon inflation fluid, and/or flushing fluid in the catheter lumens), and provides access to the needle-through lumen 14, and is typically also configured to control needle extension, retraction, and optionally rotational orientation as well. Specifically, a proximal handle at the proximal end of the needle 16 is configured for attaching to an agent source (not shown) to flow agent through the lumen 23 of the hollow needle 16 to the piercing distal tip of the needle 16, and a proximal Y-arm adapter secured to the shaft proximal end has a sidearm port 33 configured for connecting an inflation fluid source (not shown) into fluid communication with an inflation lumen 12 of the shaft for inflating the balloons 17, 18. The addition sidearm ports may be used for flushing the annular space around the needle sheath tubular member 14 and the annular space around the needle 16.

The catheter 10 is configured to be introduced into the patient's vasculature and advanced percutaneously in a low profile configuration (not shown) in which the balloons 17, 18 are deflated and optionally folded, and the needle 15 distal end is retracted into the shaft 11, to position the port 15 at the desired injection site in the patient's body lumen 30. Once at the desired injection site, the balloons are inflated and the needle distal end is slidably advanced out the port 15 and into the body lumen wall, and agent is delivered from the needle to the tissue (e.g., into the vessel wall and/or perivascular space). The needle distal tip extends radially beyond the outer profile of the inflated balloons, although the catheter is typically configured to allow the needle 16 to extend only a set limited distance away from the shaft 11, as for example by providing the catheter 10 with a needle stop member (not shown). FIG. 1 illustrates the balloons inflated against the body lumen wall, and the needle 16 partially extended in the wall of the body lumen 30. Following an injection, the needle 16 is retracted into the shaft 11 to allow the catheter 10 to be repositioned (typically with the balloons 17, 18 in a deflated configuration) or ultimately removed from the body lumen 30 at the end of the agent delivery procedure.

Figure 2:
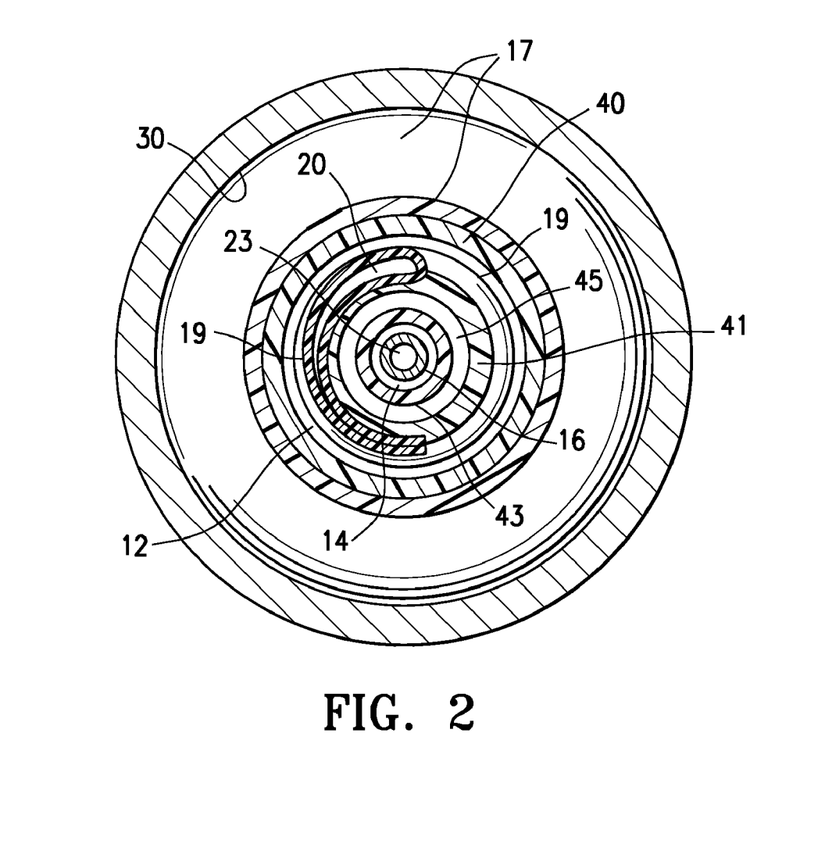
FIG. 2 is a transverse cross sectional view of FIG. 1, taken along line 2-2.
Figure 3:
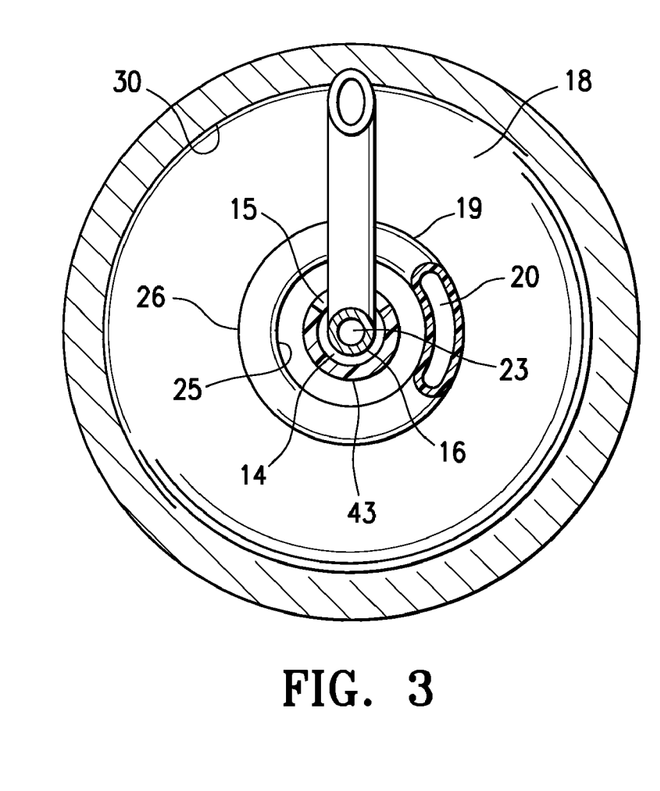
FIG. 3 is a transverse cross sectional view of FIG. 1, taken along line 3-3.

In the embodiment of FIG. 1, the shaft comprises an outer tubular member 40, an inner tubular member 41 extending within the outer tubular member, and an extension inner tubular member 42, and a needle sheath tubular member 43 disposed within the inner tubular member 41 and extension inner tubular member 42. The inflation lumen 12 is within the outer tubular member 40, and more specifically is the annular space between the inner tubular member 41 and the outer tubular member 40, as best shown in FIG. 2 illustrating a transverse cross section of FIG. 1, taken along line 2-2. The inflation lumen 12 is the single inflation lumen of the shaft, and the balloons are configured to inflate at the same time (i.e., not independently of each other). The proximal balloon 17 has a proximal skirt section sealingly secured to the distal end of the outer tubular member 40, and a distal skirt section sealingly secured to the distal end of the inner tubular member 41 such that the inflation lumen 12 opens into the inflatable interior of the proximal balloon 17, placing the inflatable interior of the proximal balloon 17 in fluid communication with the shaft inflation lumen 12. It should be noted that FIG. 2 illustrates the inflated section of the proximal balloon 17 filling the space of the body lumen 30 distal to the transverse cross section line 2-2, and FIG. 3, showing a transverse cross section of FIG. 1, taken along line 3-3, illustrates the inflated section of the distal balloon 18 filling the space of the body lumen 30 distal to the transverse cross section line 3-3. The distal balloon 18 has a proximal and distal skirt section sealingly secured to the extension inner tubular member 42. The needle-through lumen 14 is within the needle-sheath tubular member 43 and the port 15 is in a sidewall of the needle sheath tubular member 43. The needle sheath tubular member has a closed distal end with a flexible coiled distal tip 44 on the distal end of the needle sheath tubular member 43 such that the needle-through lumen 14 is a blind (closed ended) lumen. Preferably, lumen 14 is filled with material distal to port 15 to prevent air emboli and/or blood clots from forming in the distal portions of the lumen 14 and to provide a ramp to facilitate the reliable advancement of the distal end of the needle 16 out of the port 15.

In the embodiment of FIG. 1, the catheter 10 is an over-the-wire (OTW) type catheter in which the inner tubular member 41 and extension inner tubular member 42 define a wire lumen 45 therein configured to slidably receive the needle sheath tubular member 43 therein. A catheter of the invention can alternatively have a fixed-wire type shaft design as discussed in more detail below. In the embodiment of FIG. 1, the catheter 10 is typically advanced to the desired location in the body lumen 30 over a guidewire (not shown) and then the guidewire is withdrawn from the wire lumen 45 and the needle-sheath tubular member 43 slidably advanced therein (with the needle 16 retracted into the needle-through lumen 14) until the needle-through port 15 is positioned between the two balloons 17, 18 as illustrated in FIG. 1. Radiopaque markers such as marker bands 48 on the skirt sections of the balloons 17, 18, together with one or more optional additional radiopaque markers (not shown) typically provided on the needle sheath tubular member 43 (e.g., at either end of the port 15) facilitate the ability of the physician to slidably position the port 15 at the desired location between the two balloons 17, 18 under fluoroscopy. The markers 48 are also useful for positioning the balloons adjacent to the desired treatment site in the body lumen 30. The proximal end of the extension inner tubular member 42 is distally spaced from the distal end of the inner tubular member 41, thereby forming a longitudinal gap 46 in the shaft, such that the distal balloon 18 and extension inner tubular member 42 are fixedly connected to inner tubular member 41 and proximal balloon 17 only by the inflation bridge tube 19. The inflation bridge tube has sufficient stiffness to transmit longitudinal forces and torque, to ensure that the extension inner tubular member 42 is in a force and torque transmitting relationship with the inner tubular member 41, to facilitate maneuvering the catheter in the patient's tortuous vasculature. In one embodiment, the catheter shaft is reinforced with stiffening members such as small wires configured to improve this torque transmission. The inner tubular member 41, at least along a distal end section of the inner tubular member 41 within the inflatable interior of the proximal balloon 17, typically has an inner and outer diameter approximately equal to the inner and outer diameters, respectively, of the extension inner tubular member 42. In some embodiments, especially where the needle sheath outer diameter is substantially larger than the outer diameter of the desired OTW guidewire, the distal portions of extension inner tubular member 42 may be longer than is shown in FIG. 1 and have a distally reduced inner diameter and tapered outer diameter to better fit the OTW guidewire and provide an improved atraumatic distal end during OTW catheter insertion.

The inflation bridge tube 19 provides a fluid path for the inflation fluid to flow from the proximal balloon 17 to the distal balloon 18 (which would otherwise not be in fluid communication with the inflation lumen 12), in order to inflate the distal balloon 18. In the embodiment of FIG. 1, only part of the length of the inflation bridge tube 19 extends on an outer surface of the shaft 11. Specifically, the inflation bridge tube 19 has a proximal section extending along an outer surface of a section of the inner tubular member 41, and a distal section extending along an outer surface of a section of the extension inner tubular member 42. The inflation bridge tube 19 typically extends along less than the entire length of the extension inner tubular member 42, although it can alternatively extend along its entire length. An intermediate section of the inflation bridge tube 19 extends along the shaft gap 46. As a result, along the intermediate section, the inflation bridge tube 19 is not bonded to the underlying section of the shaft (i.e., the section of the needle sheath tubular member 43 slidably disposed between the two balloons 17, 18). In the embodiment of FIG. 1, the intermediate section of the inflation bridge tube 19 is radially spaced from the outer surface of the needle sheath tubular member 43 between the two balloons 17, 18, such that the intermediate section has free coil turns with an exposed inner surface 25 and an exposed outer surface 26, as best illustrated in FIG. 3.

The inflation bridge tube 19 preferably extends helically, in order to prevent or minimize any disadvantageous stiffness increase in the distal shaft section due to the presence of the inflation bridge tube. The terminology "helically" as used herein should be understood to refer generally to a spiraling configuration as in the shape of a coil, as opposed to an axially aligned member which extends substantially straight (e.g., with no intentionally induced spiraling or curving around the catheter longitudinal axis). In some embodiments, the pitch and/or coil diameter of the inflation bridge tube 19 may be adjusted based on its longitudinal position. The inflation bridge tube 19 extends helically from proximal of the proximal balloon 17 inflatable interior to distal of the distal balloon 18 inflatable interior in the embodiment of FIG. 1, and more specifically has a proximal end radially aligned with the proximal skirt section of the proximal balloon, and a distal end radially aligned with the distal skirt section of the distal balloon. As a result, a smooth transition in stiffness is provided that resists kinking at the ends of the balloons 17, 18 for improved catheter deliverability. Additionally, the helically extending inflation bridge tube 19 extending along the entire length of the inflatable interiors of the proximal and distal balloons 17, 18 increases shaft tensile break strengths (e.g., force required to separate tube 19 from shaft assembly portions 41 and 41), and reduces the risk of distal inner member 41 or extension tubular member 42 collapse or kinking by supporting the shaft wire lumen throughout the inflation section during bending. However, the ends of the inflation bridge tube 19 may alternatively be located somewhat proximal or distal to the skirt sections of the balloons. At least two adjacent coil turns along the shaft gap 46 are sufficiently spaced apart in a relaxed configuration, to provide a pathway for the needle 16 to extend through along at least a section of the shaft gap 46. The coil turns of tube 19 along the shaft gap 46 at least in one embodiment act like a spring, and under force, such as the force applied during pushing of the catheter through the vasculature, will deform by bending and shortening. Once in position such that the user is not applying a pushing or pulling force, the coil turns of tube 19 are configured to atraumatically conform to the curved vascular anatomy at least partially and to retain enough separation between coil turns to allow the needle 16 to be extended. Thus, although the coil turns of the helical inflation bridge tube 19 along the shaft gap 46 are configured at least in one embodiment to not disadvantageously longitudinally collapse (by a significant amount) as the catheter is pushed through the vasculature, the longitudinal collapse of the coil turns is expected to some degree, and some degree of collapse is advantageous in that it provides form improved flexibility and deliverability of the catheter. Additionally, the helically extending inflation bridge tube 19 is preferably formed with sufficiently stiff coil turns to transmit torque, and to minimize tightening or unwinding the coiled configuration of the tube 19 along the shaft gap 46, as the proximal end of the catheter is torqued during maneuvering of the catheter. It should be noted however that in the OTW embodiment, it is unlikely that torquing/rotation of the entire catheter is necessary or desirable, as the catheter can be positioned simply by pushing it over the OTW guidewire which is already in position. In most fixed wire-type embodiments, the entire catheter must be rotated to cause the catheter's distal tip, which is usually slightly bent, to be rotated to select the desired vascular branches during insertion to the desired site. However, in one fixed wire-type configuration, only the assembly composed of needle sheath tubular member 43 and needle 16 therein are the components attached to them need to be rotated to cause tip 44 to be rotated to select the desired vascular branches during inflation, and outer-most tubular members of the catheter assembly are not rotated relative to the anatomy (providing a less traumatic fixed wire-type configuration).

The configuration of the inflation bridge tube 19 on the shaft 11 preferably prevents or inhibits the risk of perforating or otherwise damaging the balloon or the patient's anatomy, by avoiding having abrupt, sharp edges of the tube exposed within the inflatable interior of the balloons 17, 18. In the embodiment of FIG. 1, the inflation fluid flows into and out of the lumen 20 of the inflation bridge tube 19 through the ports 21, 22 in the sidewall of the tube 19 (with arrows indicating the flow of the inflation fluid). The proximal and distal ends of the tube 19 are closed, and the sidewall ports 21, 22 may be formed by skiving or grinding a hole in the wall of the inflation bridge tube 19, as for example using a rotating cutting or grinding implement, to form a smooth edge that does not pose a significant risk of damaging the balloon wall. The inflation bridge tube 19 is at least partially embedded in the outer surface of the inner tubular member 41 and extension inner tubular member 42 in one embodiment, which creates a smooth interface with the shaft 11 along the tube 19 that significantly mitigates the risk of damaging the balloon or patient's anatomy. For example, at least in one embodiment the tube 19 has a relatively small, wire-like diameter that could otherwise form a focal stress edge that could damage the balloon wall and/or the wall of the patient's body lumen 30 if the deflated balloon length of the shaft contacts the wall of the body lumen 30 during maneuvering of the catheter 10 therein. Other methods of smoothing the tube 19 edges may be used including heat forming, applying adhesive beads, and the like. In the embodiment of FIG. 1, the entire length of the proximal and distal sections of the inflation bridge tube 19 on the inner tubular member 41 and extension inner tubular member 42 are partially embedded in the outer surface thereof, with the tube extending radially beyond the outer surface of adjacent portions of the shaft by an amount less than an outer diameter of the tube. As illustrated in FIG. 2, about half of the height of the tube 19 is embedded in the inner tubular member wall, although the tube 19 can alternatively be embedded to a greater or less degree, including being fully embedded such that the tube is flush with, or does not extend radially beyond the outer surface of adjacent portions of the inner tubular member. In one embodiment, the tube 19 is formed separately from the inner tubular members 41, 42. For example, the tube 19 may be formed of a NiTi tube that is constrained or wound in the desired coil shape on a grooved mandrel and heated to set the desired shape. The coiled tube 19 may then be embedded in the shaft by forcing the tube (in its helical configuration) over the outer diameter (OD) of the inner tubular members 41, 42, and then supporting the inner diameter affected length of the members 41, 42 with a low friction mandrel, such that the tube 19 is deformed while pressing on the OD of the members 41, 42. The assembly is typically subjected to an elevated temperature sufficient to soften the polymeric walls of the tubular members 41, 42 and allow the forces of deformed tube 19 to deform the outer walls of members 41, 42 and then the low friction mandrel is removed. In some embodiments, adhesives, such as hot melt adhesives like Primacore®, may be used (for example, applied to in liquid form, placed at in a tubing or cut tubing form, co-extruded on the OD of members 41, 42) on the interface between the coil 19 and members 41, 42 prior to heating to bond the coil 19 more securely to members 41, 42. In some embodiments, a piece(s) of heat shrink is placed over the assembly prior to heating to aid in pressing the tube 19 into members 41, 42 and to aid in forming a smooth outer surface on members 41, 42. After heating/forming, the heat shrink is removed from the assembly. However, a variety of suitable methods of providing the inflation bridge tube 19 and/or lumen 20 can be used, including molding techniques, such as insert or compression molding. The ends of the tube 19 can be closed by flattening the tube to collapse the lumen 20 at the ends and optionally bonding the collapsed inner surfaces of the tube, or plugging the ends of the tube 19 by for example applying an adhesive to fill the inner diameter at the tube 19 ends. The closed ends of the tube 19 are preferably fully embedded in the wall of the inner tubular members 41, 42, and/or covered (e.g., by the balloon skirt sections) to help ensure that the tube 19 ends do not become exposed to the anatomy and cause damage. By increasing the contact area between the inflation bridge tube 19 and the inner tubular members 41, 42, embedding the inflation bridge tube 19 improves the overall bond strength and tensile strength of the shaft. Further, embedding (partially or fully) the inflation bridge tube 19 provides a relatively low profile distal shaft section which improves catheter deliverability. Additionally, by embedding the inflation bridge tube 19, the size of the lumen 20 can be made larger relative to an inflation bridge tube that is not embedded in the shaft while still maintaining the low profile along the distal shaft section.

Although the ports 21, 22 are illustrated in FIG. 1 centered along the length of the balloons 17, 18, in alternative embodiments, the ports 21, 22 can be proximal or distal to the location illustrated in the embodiment of FIG. 1. In one embodiment, the port 21 is in the coil turn adjacent to the distal end of proximal balloon 17, and port 22 is in the coil turn adjacent to the proximal end of distal balloon 18 to shorten the fluid path length in tube 19 between the balloons 17, 18. A plug can be provided in the lumen 20 adjacent to the ports 21, 22, or the lumen 20 otherwise closed, to prevent fluid flow or pressure in the lumen 20 from stressing the structures of the closed/embedded ends of the tube 19.

The inflation bridge tube 19 provides support to the needle as the needle is extended from the shaft and into the wall of the patient's body lumen 30. Specifically, when the needle contacts the vessel wall, it creates a reactive load on the catheter body, which can force the catheter shaft away from the vessel wall and make it more difficult to puncture the vessel. The inflation bridge tube 19 limits this disadvantageous instability of the shaft, to facilitate accurate delivery of the agent to a desired injection site. For example, in the embodiment of FIG. 1, if the reactive load of the needle were to force the needle sheath tubular member 43 into contact with the lower half of the coil turns of the inflation bridge tube 19, the support provided by the inflation bridge tube 19 will limit the amount by which the needle sheath tubular member 43 further bends or flexes away from the injection site. Typically, the needle penetration force is supported by the wall of the body lumen 30, and this force is distributed over a relatively large area of the body lumen wall by the contact area of the balloons 17, 18 against the body lumen wall, such that trauma to the body lumen wall is minimized.

The coil turns of the inflation bridge tube 19, from the proximal to the distal end of the tube, are preferably spaced apart, typically by a length of at least about 0.5 to about 5 mm, more specifically about 0.3 to about 1 mm, thereby providing the catheter with flexibility along the tube 19. In one embodiment, the pitch of the coil turns varies along the length of the inflation bridge tube. For example, a first pitch of about 2 to about 5 mm provides high flexibility along the balloon inflatable interiors, whereas a second, smaller pitch (i.e., coil turns spaced apart by a smaller distance) of about 0.5 to about 2 mm between the inflatable interiors of the balloons is configured to provide a desired level of support to the needle sheath tubular member 43 during extension of the needle 16. In one embodiment, a first pitch of about 0.7 to about 1 mm is along a proximal section, and a second, smaller pitch of about 0.3 to about 0.7 mm is from the longitudinal gap 46 and distal, and provides a sufficient spacing to accommodate the extended needle.

Although discussed primarily in terms of an OTW embodiment, the catheter of Fig. could could alternatively be configured as a fixed wire-type device.

Figure 4:
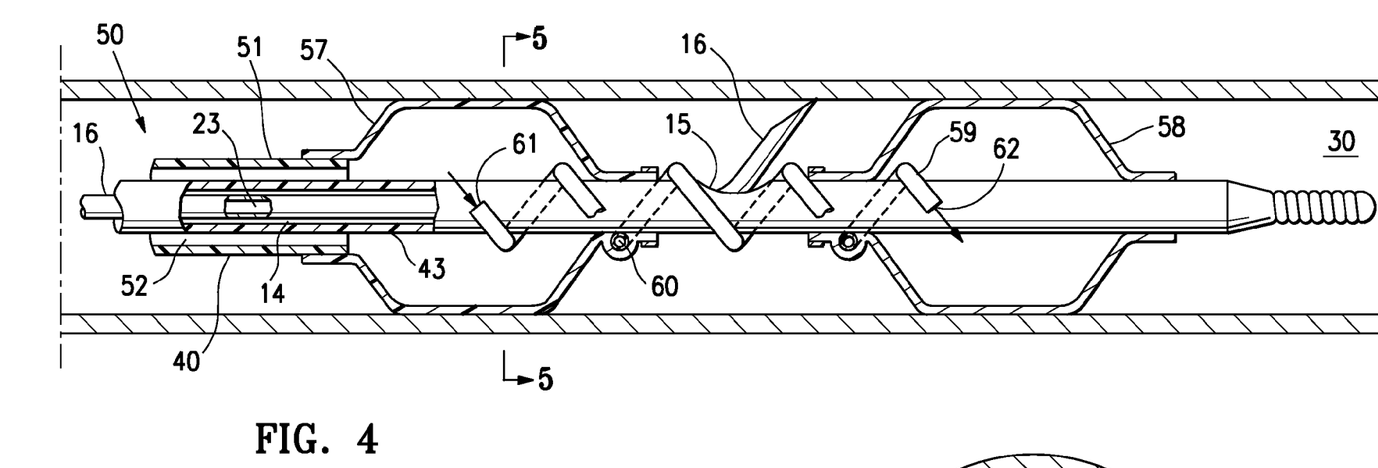
FIG. 4 illustrates a distal section of an alternative embodiment of a catheter embodying features of the invention, having an inflation bridge tube extending helically along the catheter shaft between the proximal and distal balloons and along only part of the inflatable length of each balloon.

FIG. 4 illustrates a distal section of an alternative catheter 50 embodying features of the invention. In the embodiment of FIG. 4, the shaft 51 consists essentially of the needle sheath tubular member 43 and the outer tubular member 40, and the catheter is a fixed wire-type device that is positioned at the desired treatment site in the body lumen 30 by rotating the entire catheter to have its (typically bent) distal tip select the desired vascular branches during is final positioning. Unlike the embodiment of FIG. 1, the inflation lumen 52 is the annular space between the outer tubular member 40 and the needle sheath tubular member 43, and an inflation bridge tube 59, defining inflation bridge lumen 60, is secured to the outer surface of the needle sheath tubular member 43. The needle sheath tubular member 43 extends within the outer tubular member 40 to the proximal end of the catheter 50. A proximal balloon 57 has a proximal skirt section sealingly secured to the distal end of the outer tubular member 40 and a distal skirt section sealingly secured to the needle sheath tubular member 43 proximal to the needle-through port 15, such that the inflation lumen 52 opens into the inflatable interior of the proximal balloon 57. A distal balloon 58 has a proximal and distal skirt section sealingly secured to the needle sheath tubular member 43 distal to the port 15. The catheter 50 is typically delivered to the desired site in the body lumen 30 by slidably advancing the catheter 50 in the lumen of a guiding catheter (not shown) previously introduced into the patient's anatomy, and out the distal end of the guiding catheter to accomplish its final positioning as discussed above (although in other parts of the vasculature a guiding catheter may not be used, such that the catheter is directly inserted into the introducer).

Figure 5:
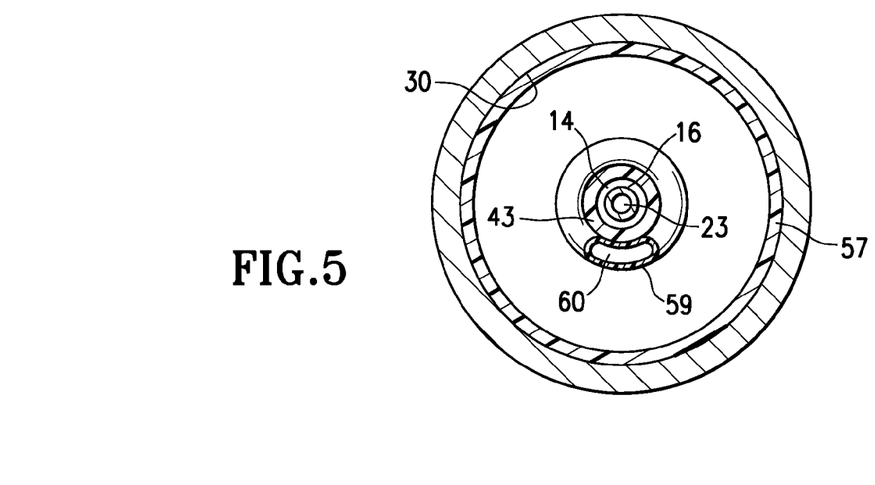
FIG. 5 is a transverse cross sectional view of FIG. 4, taken along line 5-5.

FIG. 4 illustrates the proximal and distal balloons 57, 58 inflated and the needle 16 partially extended from the needle-through lumen 14 out the port 15 in the sidewall of the needle-sheath tubular member 43. In the embodiment of FIG. 4, the inflation bridge tube 59 has a relatively short length that extends partially but not fully through the inflatable interiors of the balloons 57, 58, with the ends of the tube 59 being closer to the ends of the balloons 57, 58 adjacent to the needle-through port 15 than to the opposite ends of the balloons 57, 58. Minimizing the length of the inflation bridge tube minimizes balloon inflation/deflation times. Additionally, in the illustrated embodiment, the inflation bridge tube 59 is not embedded in the shaft 51 (i.e., the needle sheath tubular member 43). Rather, the inflation bridge tube 59, bonded to the outer surface of the needle sheath tubular member 43, extends radially beyond the outer surface of the needle sheath tubular member 43 by an amount equal to substantially the entire outer diameter of the tube 59. Due to the configuration of the needle sheath tubular member, which typically has a relatively small wall thickness, and which, in one embodiment, is formed of a metal, the inflation bridge tube 59 is typically not embedded (fully or partially) along all or part of its length in the outer surface of the needle sheath tubular member 43. Ports 61, 62 in the open ends of the inflation bridge tube 59 allow the inflation fluid to flow between the inflatable interiors of balloon 57 and distal balloon 58 during balloon inflation/deflation. In an alternative embodiment, the inflation bridge tube 59 extends on the needle sheath tubular member 43 through all or at least a majority of the length of the inflatable interiors of the balloons, and/or has closed distal ends and sidewall ports spaced between the ends of the tube 59, similar to the embodiment of FIG. 1. FIG. 5 illustrates a transverse cross section of FIG. 4, taken along line 5-5.

Figure 6:
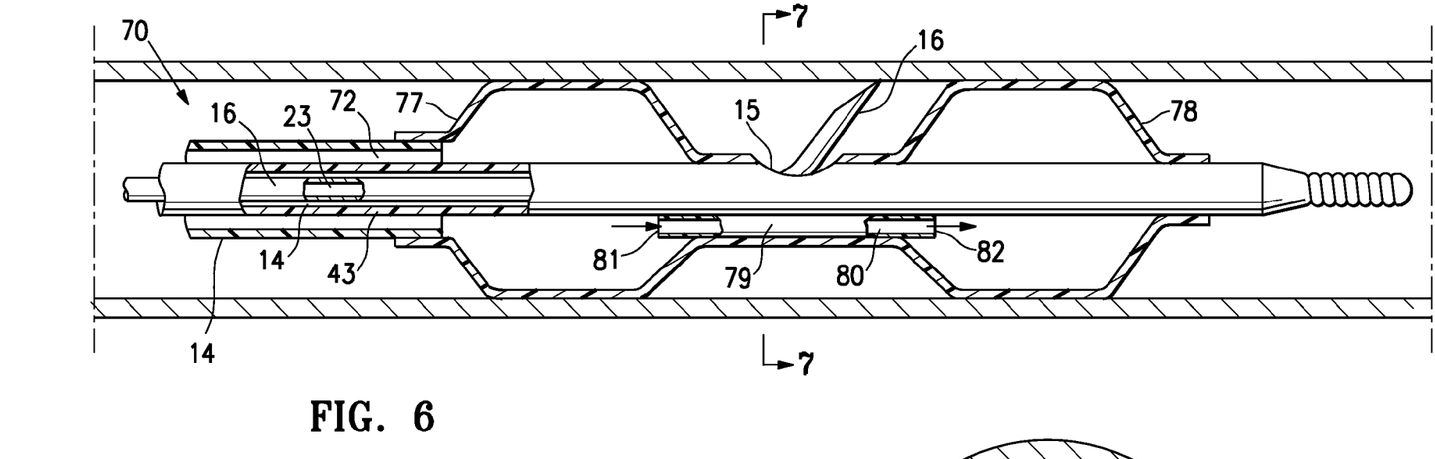
FIG. 6 illustrates a distal section of an alternative embodiment of a catheter embodying features of the invention, having an inflation bridge tube extending in a generally axial direction along the catheter shaft between the proximal and distal balloons and along only part of the inflatable length of each balloon.
Figure 7:
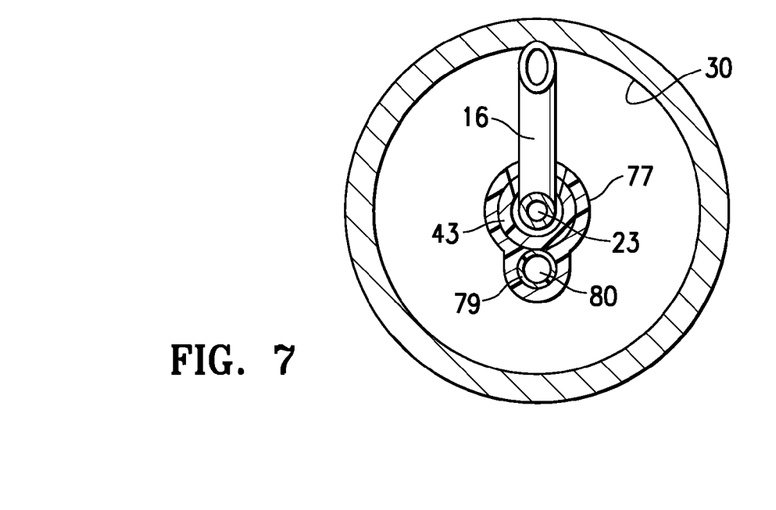
FIG. 7 is a transverse cross sectional view of FIG. 6, taken along line 7-7.

FIG. 6 illustrates a distal section of an alternative catheter 70 embodying features of the invention, in which a proximal balloon 77 and a distal balloon 78 are sealingly secured to the needle sheath tubular member 43 similar to the embodiment of FIG. 4, and the inflation lumen 72 is the annular space between the outer tubular member 40 and the needle sheath tubular member 43 therein. In the embodiment of FIG. 6, an inflation bridge tube 79, defining inflation bridge lumen 80, extends in a generally axial (longitudinal) direction along the outer surface of the needle sheath tubular member 43. The longitudinally extending inflation bridge tube 79 provides for ease of manufacture, as well as greater pushability and faster inflation/deflation response times, and kink resistance at the kink point caused by port 15 in the wall of the needle sheath 43. FIG. 7 illustrates a transverse cross section of the FIG. 6, taken along line 7-7. In the embodiment illustrated in FIG. 6, the inflation bridge tube 59 has a relatively short length that extends partially but not fully through the inflatable interiors of the balloons 77, 78, with ports 81,82 in the open ends of the inflation bridge tube 43, as discussed above in relation to the embodiment of the FIG. 4. The axially extending inflation bridge tube 79 can alternatively extend through all or at least a majority of the length of the inflatable interiors of the balloons 77, 78, and/or have closed distal ends and sidewall ports spaced between the ends of the tube 79, similar to the embodiment of FIG. 1. FIG. 6 illustrates the balloons 77, 78 inflated into contact with the wall of the body lumen 30, and the needle 16 only partially extended from the needle-through lumen 14 out the port 15. The balloons 77, 78 are sufficiently close together that the distal skirt section of the proximal balloon 77 and the distal skirt section of the distal balloon 78 extend along the section of the needle sheath tubular member 43 having the port 15 therein, such that the wall of the balloon skirt sections is typically cut or otherwise perforated to form a passageway at the port 15 for lateral egress of the needle 16.

Although discussed primarily in terms of needle catheters having a needle slidably disposed in the catheter shaft for injecting an agent into a patient's body lumen wall, it should be understood that a catheter of the invention can be configured for a variety of suitable uses, including providing for agent delivery by infusing an agent into the patient's anatomy adjacent to or in the vicinity of the lumen, and through an agent delivery port in the catheter shaft. A catheter of the invention could also be used as an aspiration catheter or embolic protection device, for example to aspirate hematocrit and emboli from a vessel segment. In the illustrated embodiments, the balloons inflate coaxially around the circumference of the shaft, although a variety of suitable balloon configurations can be used including balloons eccentrically mounted on the catheter shaft (e.g., eccentric balloons such that the port 15 may be pressed up against the vessel wall during balloon inflation, more tightly controlling the needle penetration length into the lumen wall), or balloons that extend in a spiral or curvilinear fashion about the catheter shaft. In the illustrated embodiments, each balloon has a radially expanded inflated configuration which extends around the circumference and along an outer surface of the shaft to position the shaft at the port spaced away from the body lumen wall in the expanded configuration, such that the needle slidably exits the needle-through lumen in the extended configuration through the port spaced away from the body lumen wall. In a presently preferred embodiment, the balloons are configured such that the shaft at the needle port 15 is substantially centered in the body lumen 30 by the inflated balloons. Although not illustrated, catheters of the invention can be configured to provide a perfusion pathway that allows fluid, e.g., blood, flow in the body lumen 30 across the inflated balloons such that the inflated balloons do not completely occlude the body lumen 30 during an agent delivery procedure.

A variety of suitable agents can be delivered using a catheter and method of the invention. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. Suitable therapeutic agents include, but are not limited to, thrombolytic drugs, anti-inflammatory drugs, anti-proliferative drugs, drugs restoring and/or preserving endothelial function, and the like. A variety of bioactive agents can be used including but not limited to peptides, proteins, oligonucleotides, cells, and the like. The agent is typically a therapeutic agent for restenosis, although the agent can be delivered for a variety of treatment procedures, including treatment of a diseased (occluded) blood vessel by delivery of the agent directly to the diseased blood vessel, or treatment of the myocardium of the heart by delivery of an agent directly into the adjacent myocardium, the pericardial sac, and/or in the pericardial space around the vessel. In a presently preferred embodiment, the agent is an anti-inflammatory agent including steroids, or is an agent that induces cholesterol efflux from arterial wall plaque including ApoA1 mimetic peptides, PPARα agonists. In one embodiment, the catheter is used to deliver an agent into organ tissue, such as renal, spleen, liver, or stomach tissue, or any body organ with vasculature that runs near a target treatment site. The agent(s) can be delivered directly into the organ tissue adjacent to a disease. Suitable agents include anti-proliferative, anti-inflammatory, anti-neoplastic, anti-platelet, anti-coagulant, anti-fibrin, anti-thrombotic, anti-mitotic, antibiotic, anti-allergic, and antioxidant compounds. For example, in one embodiment, the catheter is used to deliver therapeutic agent microparticles into renal tissue. Modifications to the catheter device components may be required to produce a device that operates within different organ vascular systems, for example by reducing or enlarging the size of the device for use in body lumens that are smaller or larger relative to typical coronary vessels. In addition to therapeutic agents, a variety of diagnostic agents can be used according to the present invention. The agent may be provided in a variety of suitable formulations and carriers including liposomes, polymerosomes, nanoparticles, microparticles, lipid/polymer micelles, and complexes of agents with lipid and/or polymers, and the like.

The dimensions of catheters 10, 50, 70 depend upon factors such as the catheter type, and the size of the artery or other body lumen through which the catheter must pass. By way of example, the needle sheath tubular member typically has an outer diameter of about 0.014 to about 0.016 inch, and an inner diameter of about 0.010 to about 0.012 inch. The shaft inner tubular member 41 configured to slidably receive the needle sheath tubular member 43 typically has an outer diameter of about 0.022 to about 0.26 inch (0.56 to 0.66 mm), and an inner diameter of about 0.016 to about 0.018 inch (0.41 to about 0.46 mm). The outer tubular member 40 typically has an outer diameter of about 0.036 to about 0.040 inch (0.91 to 1.0 mm), and an inner diameter of about 0.028 to about 0.032 inch (0.71 to 0.81 mm). The balloons on this embodiment generally have a length of about 4 to about 6 mm, and radially expand to a maximum outer diameter of about 2.0 to about 4.0. Typically, for coronary arteries, the balloons radially expand to a maximum outer diameter of about 2.0 to about 4.0 mm, and have a length of about 8 to about 30 mm. The overall length of the catheter may range from about 100 to about 150 cm, and is typically about 143 cm.

The inflation bridge tube 19, 59, 79 is typically formed of a metallic tube such as a NiTi alloy or stainless steel (which allows for a thin wall and low profile), or a polymeric material such as a polyethylene, polyvinyl chloride, polyester, polyamide, polyimide, polyurethane, and copolymers thereof, or composite materials, and is secured to the shaft by adhesive and/or heat fusion bonding. A hot melt adhesive such as PRIMACOR® is useful for securing polymeric components to a metallic inflation bridge tube. The needle sheath tubular member 43 is preferably formed of metal such as a nickel-titanium alloy (NiTi) and/or stainless steel, although it can alternatively or additionally be formed of suitable plastics commonly used in catheter shaft construction such as polyamides, polyurethanes, silicone modified polyurethanes, fluoropolymers, polyolefins, polyimides. In one embodiment, the needle sheath tubular member 43 has a proximal section of stainless steel joined to a distal section of NITINOL. In one embodiment the needle 16 has a distal section of NiTi joined to a proximal section of stainless steel, although the needle can alternatively be formed of a single material/tubular member, including polymeric materials.

The shaft tubular members can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. A variety of suitable shaft configurations can be used including one or more of the tubular members formed of single or multiple layers or sections of tubing, as are conventionally known for catheter shaft design Although discussed primarily in terms of catheters in which the needle extends from within needle sheath tubular member, catheters having the inflation bridge tube in accordance with the invention can have a variety of suitable shaft designs. Additionally, the term "catheter" should be understood to refer to a variety of device designs generally having an elongated structure configured for percutaneous advancement through a patient's vasculature. While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

We claim:

1. An agent delivery catheter configured for delivering an agent to an injection site in a wall of a patient's body lumen, comprising:
   a) an elongated shaft having a proximal end, a distal end, an inflation lumen located within the elongated shaft and extending distally from the proximal end of the shaft to a distal end located proximal to the distal end of the catheter shaft, a needle-through lumen slidably containing a needle therein, and at least one needle-through port such that the needle has a retracted and an extended configuration;
   b) a proximal balloon on a distal shaft section with an inflatable interior located proximal to the needle-through port, sealingly secured to the shaft adjacent to the distal end of the inflation lumen such that the proximal balloon inflatable interior is in fluid communication with the inflation lumen, and a distal balloon on the shaft distal to the proximal balloon with an inflatable interior located distal to the needle-through port; and
   c) a tube defining an inflation bridge lumen, external to said elongated shaft and extending between the inflatable interiors of the balloons from a location proximal to a location distal of the needle-through port, and having a proximal port within the proximal balloon interior, and a distal port within the distal balloon interior, to thereby provide for inflation of the distal balloon by placing the distal balloon interior in fluid communication with the proximal balloon interior.

2. The catheter of claim 1 wherein the inflation bridge tube extends helically between the inflatable interiors of the balloons.

3. The catheter of claim 2 wherein the inflation bridge tube extends along substantially an entire length of the inflatable interiors of the balloons.

4. The catheter of claim 2 wherein the inflation bridge tube is partially embedded in an outer surface of the shaft such that the tube extends radially beyond the outer surface of adjacent portions of the shaft by an amount less than an outer diameter of the tube.

5. The catheter of claim 2 wherein the inflation bridge tube has a closed proximal end, such that the inflation bridge proximal port is located in a side wall of the tube distal to the closed proximal end.

6. The catheter of claim 5 wherein the inflation bridge tube has a closed distal end, such that the inflation bridge distal port is located in a side wall of the tube proximal to the closed distal end.

7. The catheter of claim 6 wherein the inflation bridge tube extends from a location proximal to the proximal balloon inflatable interior to a location distal to the distal balloon inflatable interior.

8. The catheter of claim 2 wherein the inflation bridge tube has an intermediate section between the two balloons which has free coil turns with exposed inner and outer surfaces.

9. The catheter of claim 1 wherein at least a section of the inflation bridge tube extends substantially axially on an outer surface of the shaft.

10. An agent delivery catheter configured for delivering an agent to an injection site in a wall of a patient's body lumen, comprising:
  a) an elongated shaft having a proximal end, a distal end, an inflation lumen extending distally from the proximal end of the shaft to a distal end located proximal to the distal end of the catheter shaft, a needle-through lumen slidably containing a needle therein, and at least one needle-through port such that the needle has a retracted and an extended configuration;
  b) a proximal balloon on a distal shaft section with an inflatable interior located proximal to the needle-through port, sealingly secured to the shaft adjacent to the distal end of the inflation lumen such that the proximal balloon inflatable interior is in fluid communication with the inflation lumen, and a distal balloon on the shaft distal to the proximal balloon with an inflatable interior located distal to the needle-through port; and
  c) a tube defining an inflation bridge lumen, external to said elongated shaft and extending between the inflatable interiors of the balloons from a location proximal to a location distal of the needle-through port, and having a proximal port within the proximal balloon interior, and a distal port within the distal balloon interior, to thereby provide for inflation of the distal balloon by placing the distal balloon interior in fluid communication with the proximal balloon interior, the inflation bridge tube extending helically between the inflatable interiors of the balloons, wherein the inflation bridge tube has an intermediate section between the two balloons extending along a gap in the shaft, the shaft having an inner tubular member with a distal end sealingly secured to a distal end of the proximal balloon, and an extension inner tubular member which has the distal balloon sealingly secured thereto and which is distally spaced from the distal end of the inner tubular member thereby forming the shaft gap, such that the distal balloon and extension inner tubular member are fixedly connected to inner tubular member and proximal balloon only by the intermediate section of the inflation bridge tube.

11. The catheter of claim 10 wherein the shaft includes a needle sheath tubular member defining the needle-through lumen and port, and an outer tubular member having the inflation lumen therein, and the inner tubular member and extension inner tubular member define a wire lumen configured to slidably receive the needle sheath tubular member therein.

12. The catheter of claim 11 wherein the inflation bridge tube extends helically along its entire length, with a proximal section extending helically around a section of the inner tubular member and a distal section extending helically around at least a section of the extension inner tubular member.

13. A balloon catheter, comprising:
  a) an elongated shaft having a proximal end, a distal end, an inflation lumen located within the elongated shaft, a wire lumen, a distal shaft section with the wire lumen therein extending to a port in the distal end of the distal shaft section, and an extension inner tubular member which defines a distal section of the wire lumen and which is distally spaced from the distal end of the distal shaft section such that there is a gap in the shaft;
  b) a proximal balloon on the distal shaft section with an inflatable interior located proximal to the shaft gap, sealingly secured to the shaft adjacent to the distal end of the inflation lumen such that the proximal balloon inflatable interior is in fluid communication with the inflation lumen, and a distal balloon on the extension inner tubular member with an interior located distal to the shaft gap; and
  c) a tube defining an inflation bridge lumen external to the elongated shaft, extending helically at least between the inflatable interiors of the balloons, and having a proximal port within the proximal balloon interior and a distal port within the distal balloon interior to thereby provide for inflation of the distal balloon by placing the distal balloon interior in fluid communication with the proximal balloon interior.

14. The catheter of claim 13 wherein the catheter is a needle catheter having a needle sheath tubular member which is slidably disposed in the wire lumen, and which has a needle-through lumen slidably containing a needle therein, and at least one needle-through port configured to allow the needle to be extended out the port and between spaced apart turns of the helical inflation bridge tube between the balloons.

15. The catheter of claim 13 wherein the inflation bridge tube extends along substantially an entire length of the inflatable interiors of the balloons.

16. The catheter of claim 15 wherein the inflation bridge tube is at least partially embedded in an outer surface of the shaft.

* * * * *